United States Patent [19]
Grob et al.

[11] Patent Number: 5,009,064
[45] Date of Patent: Apr. 23, 1991

[54] APPARATUS FOR MEASURING THE PARTICULATE MATTER IN THE FLUE GAS OR EXHAUST GAS FROM A COMBUSTION PROCESS

[75] Inventors: Ferdinand Grob, Besigheim; Dieter Kienzler, Stuttgart; Ernst Linder, Muehlacker; Roger Potschin, Marbach; Heinz Stutzenberger, Vaihingen/Enz, all of Fed. Rep. of Germany

[73] Assignee: Robert Bosch GmbH, Stuttgart, Fed. Rep. of Germany

[21] Appl. No.: 424,463

[22] Filed: Oct. 20, 1989

Related U.S. Application Data

[63] Continuation-in-part of Ser. No. 254,623, Oct. 7, 1988, Pat. No. 4,922,714.

[30] Foreign Application Priority Data

Nov. 23, 1987 [DE] Fed. Rep. of Germany ....... 3739622
Nov. 22, 1988 [DE] Fed. Rep. of Germany ....... 3839348

[51] Int. Cl.$^5$ ............................................... F01N 3/00
[52] U.S. Cl. ......................................... 60/276; 73/116
[58] Field of Search ........................... 60/276; 73/116

[56] References Cited

U.S. PATENT DOCUMENTS

| 3,362,387 | 1/1968 | Neumann | 60/276 |
| 3,384,746 | 5/1968 | Benz | 73/116 |
| 4,501,138 | 2/1985 | McCandless | 73/116 |

Primary Examiner—Douglas Hart
Attorney, Agent, or Firm—Edwin E. Greigg

[57] ABSTRACT

An apparatus for measuring particulate matter in a flue gas or exhaust gas of a combustion process comprising means for transmitting a beam of light between an optical transmitter and an optical receiver. The light passes through two diametrically opposed light slits closed by transparent bodies in the wall of the tail pipe and crosses through a flow of exhaust gas carried in the tail pipe. The attenuation of intensity of the light beam is a measure of the particulate matter. When the measuring apparatus is used to measure a soot concentration in an exhaust gas of internal combustion engines of a vehicle, it is mounted directly on the tail pipe, and the transparent bodies are heated in the vicinity of the faces acted upon by the exhaust gas flow to a temperature above the soot burn-off temperature. As a result, adulteration of the measured value by soot deposits in the measurement path to the transparent bodies is prevented, and continuous operation of the measuring apparatus is assured.

21 Claims, 4 Drawing Sheets

APPARATUS FOR MEASURING THE PARTICULATE MATTER IN THE FLUE GAS OR EXHAUST GAS FROM A COMBUSTION PROCESS

RELATED PATENT APPLICATION

This application is a continuation-in-part of application Ser. No. 254,623 filed Oct. 7, 1988, now U.S. Pat. No. 4,922,714.

BACKGROUND OF THE INVENTION

The invention relates to an apparatus for measuring the particulate matter in the flue gas or exhaust gas from a combustion process.

In a measuring instrument of this kind, the light emitted by an optical transmitter passes through the exhaust pipe and is converted by an optical receiver into an electrical signal. The particles located in the exhaust gas lead to a decrease in the amount of light, which is expressed as extinction or turbidity and is a standard for the soot emission of a combustion device.

In a known apparatus of this kind (German Utility Model 81 28 634), bodies transparent to light are made in the form of windows, each closing off a passage, inserted into the light opening or slit, spaced apart from the tubular wall of the exhaust pipe. The result is a hydraulically idle volume in front of each window, which causes considerable deposits of particles on the windows. To eliminate the measurement errors originating in the dirt on the windows, one window has a retroreflector associated with it, which is protected in a chute against being soiled and is located outside the beam of light. At certain time intervals, the reflector is briefly moved into the beam path. It then reflects the beam of light from the optical transmitter that passes through the window back to the optical receiver. There a signal is obtained that is equivalent to the reduction in transmission caused by soiling of the window and provides a correction value for further measurement once the retroreflector is removed. This kind of recalibration of the measuring instrument is complicated and is suitable only for stationary combustion systems, but not for mobile ones such as internal combustion engines in motor vehicles.

In internal combustion engines equipped with fuel injection pumps, such measuring equipment is used so that from the soot concentration in the exhaust gas, a control variable for fuel injection is derived, with which the full-load injection quantity can be metered in such a way that the maximum soot emission prescribed by law is not exceeded (U.S. Pat. No. 3,744,461).

In a known measuring instrument for internal combustion engines (British Patent 1,334,472), an electrical detector is installed on the circumference of the exhaust pipe carrying the flow of exhaust gas, and the detector receives the signal from an electrical transmitter that is likewise disposed on the circumference of the exhaust pipe, directly opposite the detector. The intensity of the signal received by the detector increases or decreases—depending on the type of detector—whenever the soot concentration in the exhaust gas flow increases. The electrical output signal of the detector is amplified and forms a direct control signal for adjustment of a valve. For maximum prevention of adulteration of the measurement from soot concentration on the detector and transmitter, a curtain of flushing air is installed between the exhaust gas, on the one hand, and the active elements of the detector and transmitter, on the other. Nevertheless, soot deposits on the active elements cannot be prevented, so that over the long term a drift in the measurement values occurs.

OBJECT AND SUMMARY OF THE INVENTION

The apparatus according to the invention has an advantage as with the measuring apparatus for stationary combustion systems, the transparent bodies prevent direct deposits of soot on the active elements of the transmitter and receiver; but in contrast to these combustion systems, the transparency of the bodies is assured by avoiding soot deposition, by means of the heater. This prevents other factors besides the soot concentration in the exhaust gas from causing turbidity, and hence adulterating the measurement signal, in the optical signal received. Calibration measurements can be dispensed with. Continuous, interruption-free operation is assured. The transparent bodies may be embodied as disks or bars of sapphire or quartz, which are sintered, cemented or pressed in the ceramic bodies. In individual cases, especially with disks or bars that are flush with the exhaust pipe, the prevention of soiling of the transparent bodies can be further reinforced by providing, in a feature of the invention, that the bodies are acted upon, on their surface facing into the flow of exhaust gas, with pulses of flushing air.

Substantial advantages of the apparatus are attained in that in a preferred embodiment of the invention, the optical transmitter and receiver are connected to the one light slit via fiber optical wave guides; a reflection surface is disposed behind the other light slit, and the transparent bodies are located between the wave guide and the reflection face, and between the wave guide and the flow of exhaust gas, respectively. With these provisions, the length of the beam of light penetrating the flow of exhaust gas is doubled while the diameter of the exhaust pipe is unchanged; thus greater measurement accuracy is attained without enlarging the exhaust pipe. The reflection face may advantageously be formed by a retroreflector, which in turn is embodied by the suitably shaped, heated sapphire or quartz body. A separate fiber optical wave guide leads from the optical transmitter and the optical receiver to the one light slit. Both wave guides terminate in a common terminal piece. The undesirable reflection from the transmitted light on the side oriented toward the transmitter wave guide can be reduced by embodying the transparent body as a double cone.

In a further feature of the invention, if the emitted light is divided into a measurement beam and a reference beam, then the temperature drift, aging and other harmful effects of a light emitting diode or LED forming the light source of the optical transmitter can be detected and compensated for in an evaluation circuit. If the reference diode is disposed in the receiver, then a third fiber optical wave guide must couple the reference diode to the transmitter. If the reference diode is disposed in a side channel behind the transmitter diode, the third fiber optical wave guide can be omitted.

The aforementioned pulses of flushing air are advantageously made available, in a further feature of the invention by a diaphragm pump that is driven by the pressure pulses of the exhaust. Thus, the flushing air supply requires no additional energy.

The measurement apparatus can be embodied structurally simply and economically if, in a preferred feature of the invention, a heating coil is applied directly to the transparent bodies, which are embodied as glass rods. The ceramic bodies can then be omitted as supports for the heating coils, which translates into reduced production costs. The glass rods are then preferably manufactured from quartz glass.

The embodiment of the transparent bodies as elongated glass rods also makes it possible, in a further advantageous feature of the invention, to dispose the transmitter and receiver directly on the exhaust pipe, and thus to dispense with the fiber optical wave guides. This further reduces the production costs. Accommodating the optical transmitter and receiver on the same side of the exhaust pipe and disposing a retroreflector on the other side of the exhaust pipe is extremely advantageous from the standpoint of control technology and also makes it possible to provide a compact structure of the measuring instrument.

A structural simplification is attained if in a further feature of the invention the LED, a photoelectric diode and a reference photoelectric diode are disposed on a common substrate. Then the finished diodes can be cast on the substrate, or the semiconductors can be bonded to the substrate. A mirror or a metal wafer provides shielding of light between the adjacent transmitter and receiver diodes.

The invention will be better understood and further objects and advantages thereof will become more apparent from the ensuing detailed description of preferred embodiments taken in conjunction with the drawings.

DESCRIPTION OF THE EXEMPLARY EMBODIMENTS

Figure 1:
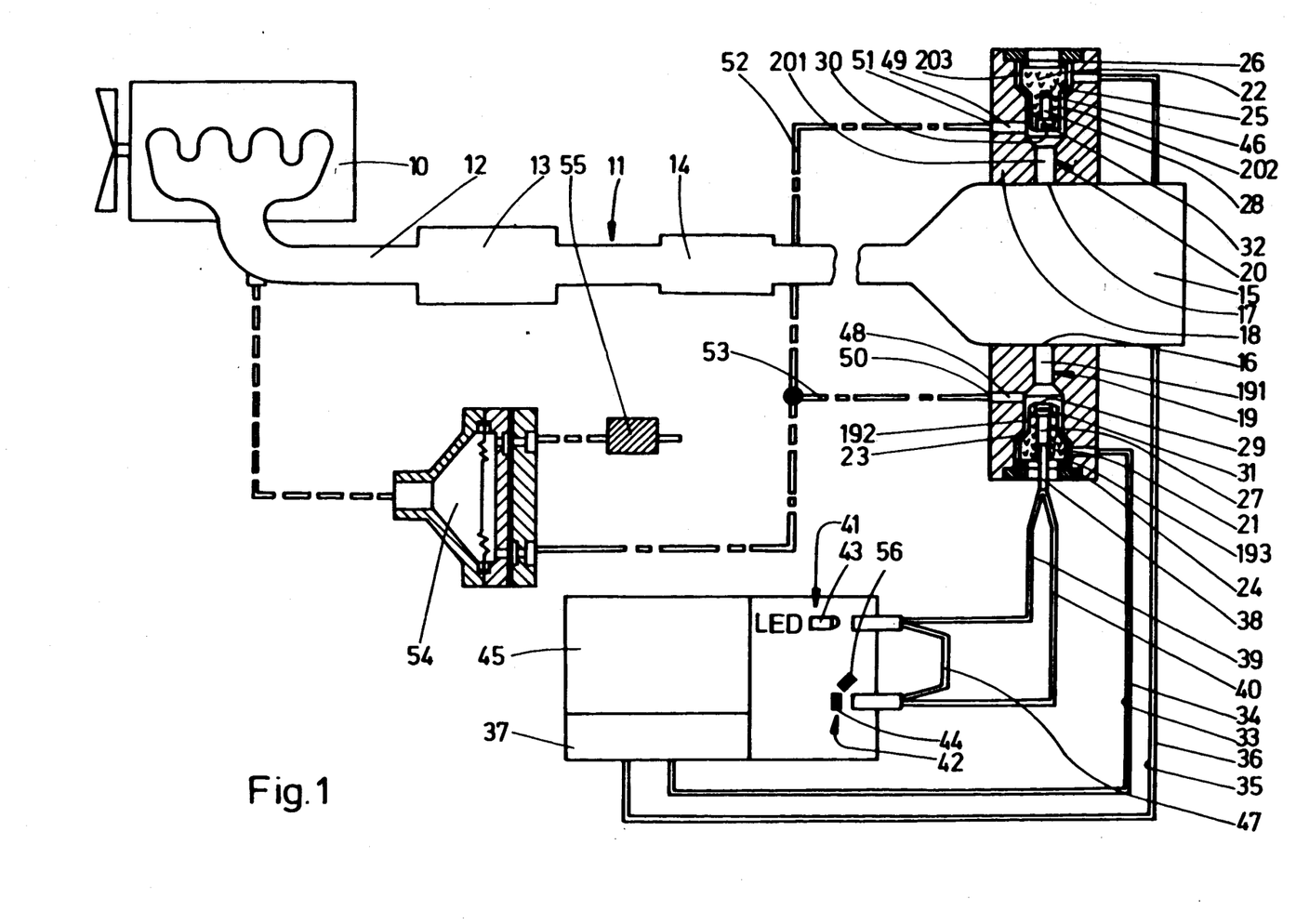
FIG. 1 shows an engine of a motor vehicle, in block form, with its exhaust system and an apparatus connected to it for measuring the soot concentration in the exhaust gas.

In FIG. 1, an internal combustion engine 10 is shown, in particular a Diesel engine, of a motor vehicle, serving as an example of an internal combustion engine; the exhaust system 11 is attached to the engine 10. The exhaust system comprises the pipe 12 carrying exhaust gas, which includes one or two mufflers 13, 14, and a tail pipe 15. The apparatus for measuring the soot concentration in the flow of exhaust gas through the tail pipe 15 is disposed on the tail pipe 15. To this end, the wall of the tail pipe 15 is provided with two diametrically opposed light slits 16, 17, and in the vicinity of these light slits 16, 17 the tail pipe is surrounded by an attachment ring 18, which has radial bores 19, 20 in alignment with the light slits 16, 17. The radial bores 19, 20 are embodied as stepped bores with the bore diameter of the various bore sections 191-193 and 201-203 increasing from the tail pipe 15 outward up to the outer circumference of the attachment ring 18. A ceramic body 21 or 22 is inserted into the two outer bore sections 192, 193 or 202 and 203, respectively and adapted to the contours of the respective bore sections 192, 193 or 202, 203. The annular gap remaining between the ceramic bodies 21, 22 and the bore sections 192, 193 or 202, 203 is sealed with ring seals 23, 24 and 25, 26, respectively, so that no exhaust gas can flow out of the attachment ring 18. Each ceramic body 21, 22 has an axial bore, which is embodied as a through bore 27 for the ceramic body 21 and as a blind bore 28 for the ceramic body 22. Both the through bore 27 and the blind bore 28 discharge on the face end of the ceramic body 21 and 22, respectively, oriented toward the tail pipe 15, and are there closed off by a transparent disk in the form of a sapphire disk 29, 30 sintered into the ceramic bodies 21 and 22. A platinum heating coil schematically represented at 31 and 32 is disposed on the ceramic bodies 21 and 22 and connected to two respective connection wires 33, 34 and 35, 36, which lead to a heating circuit 37. With these platinum heating coils 31, 32, the sapphire disks 29, 30 are heated to a temperature that is above the soot burn-off temperature, so that soot can no longer settle on the sapphire disks 29, 30, and so the transparency of the sapphire disks 29, 30 remains assured.

A fiber optical wave guide terminal piece 38, which joins two fiber optical wave guides 39, 40, is inserted into the through bore 27 of the ceramic body 21. One wave guide 39 leads to an optical transmitter 41, and the other wave guide 40 leads to an optical receiver 42. In the optical transmitter 41, a light source embodied as a light-emitting diode or LED 43, is coupled to the wave guide 39. In the optical receiver 42, the wave guide 40 is optically coupled with a photodetector, here a simple photoelectric diode 44. The receiver 42 is connected to an evaluation circuit 45, which from the light intensities retrieved, with turbid and unturbid light passed through the exhaust pipe, calculates an absorption coefficient K or the turbidity T and compares it with rpm-dependent threshold values stored in a performance graph. Deviations from setpoint values are used as control variables to correct the quantity adjusting device of the fuel injection pump. The light emitted by the LED 43 is pulsed, which compensates for the effect of scattered light from the environment and the thermal radiation of the hot sapphire disks 29, 30. The wavelength of the light is preferably in the infrared range, on the one hand because infrared detectors with an elevated light yield are available, and on the other hand because with infrared light, the influence on the measurement result on the particle size in the exhaust gas is less.

A reflection face 46 in the form of a retroreflector foil is disposed on the bottom of the blind bore 28 in the ceramic body 22, so that the light originating in the optical transmitter 41, which is carried via the wave guide 39 into the attachment ring 18, crosses the tail pipe 15, is reflected at the reflection face 46, passes once again through the tail pipe 15, and is then carried via the wave guide 40 to the optical receiver 42. As a result, the beam of light crosses the flow of exhaust gas in the tail pipe 15 twice, so that the measurement path that detects the soot concentration is twice as long as the diameter of the tail pipe 15. A third fiber optical wave guide 47 leads directly from the transmitter 41 to the receiver 42, where it acts upon a reference diode 56. By means of this arrangement, the light emitted by the LED 43 is divided into a measurement beam, transmitted via the wave guide 39, and a reference beam, transmitted via the wave guide 47. As a result, fluctuations in intensity of the LED 43 can be compensated for in a simple manner in the evaluation circuit 45.

Two axial bores 48, 49 extending at right angles to the radial bores 19, 20 are provided in the attachment ring 18, each extending into one of the radial bores 19, 20, in the vicinity of the second bore section 192 or 202. The axial bores 48, 49 are provided with a flushing air connection 50 or 51, which discharges into the radial bores and these connections communicate via flushing air lines 52, 53 with a diaphragm pump 54. The diaphragm pump 54, the structure of which is known per se, communicates with the exhaust pipe 12 and is driven by the pressure pulses of the exhaust gases. The air aspirated via an air filter 55 is forced into the bore sections 192 and 202 in the form of pressure pulses via the flushing air lines 52, 53, and in these bore sections acts upon the sapphire disks 29, 30. This provides additional cleaning action on the sapphire disks 29, 30. The flushing air is delivered to the tail pipe 15 via the bore sections 191 and 201 and leaves the tail pipe along with the flow of exhaust gas.

The above-described apparatus for measuring the soot concentration in the engine exhaust gas functions as follows:

From the LED 43, light is emitted at a defined light intensity $\phi^*$. The beam of light exits the terminal piece 38 of the wave guide 39, passes through the light slit 16, crosses the exhaust gas flow, and passes through the light slit 17 onto the reflection face 46. The light beam is reflected there and takes the same course in the opposite direction back to the terminal piece 38, and from there, via the wave guide 40, reaches the photoelectric diode 44 of the optical receiver. After passing twice through the exhaust gas flow, the beam of light is received in the photoelectric diode 44 with an intensity $\phi_0$, and if there is a given soot concentration it is received as more or less turbid at an intensity $\phi$. The intensity $\phi$, according to Beer-Lambert's law, depends on the length of the measurement path L, in this case twice the diameter of the exhaust pipe; on the absorption properties K of the exhaust flow; and on the received intensity $\phi_0$ of the light if the exhaust gas is pure, in accordance with the following equation:

$$\phi = \phi_0 e^{-K \cdot L}$$

In the evaluation circuit, from the known received intensity $\phi_0$ of the beam of light with pure exhaust gas and from the light intensity $\phi_0$ measured at the photoelectric diode 44, the absorption coefficient K or the turbidity T is calculated in accordance with the following equation $$T = 1 - \frac{\phi}{\phi_0} = 1 - e^{-K \cdot L}$$

The turbidity T is compared with rpm-dependent threshold values stored in a performance graph. Deviations in the actual value are compensated for by displacement of the governor rod of the fuel injection pump, which varies the fuel injection quantity. Heating the sapphire disks 29, 30 and acting upon them with flushing air protects the optical systems against soiling, so that no adulteration of the measured value arises.

Figure 2:
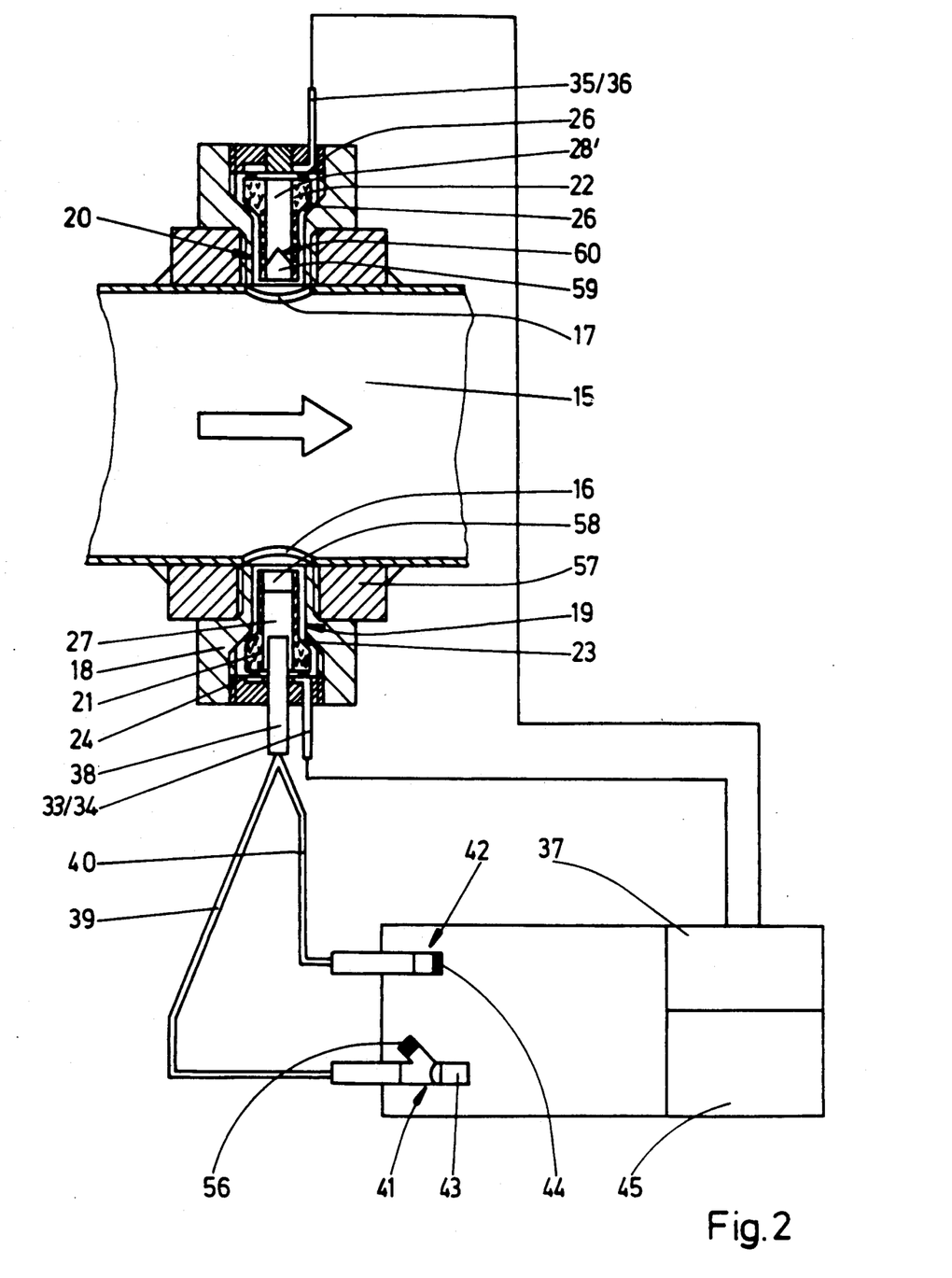
FIG. 2 shows in detail showing an exhaust pipe of the exhaust system of FIG. 1, with a measuring apparatus in a further exemplary embodiment.

The measuring apparatus shown in FIG. 2 is in principle identical to what is described above, except that some advantageous modifications have been made. The attachment ring 18 is secured to the tail pipe 15 by means of a ring carrier or welded-on stopper 57. The ceramic bodies 21, 22 are inserted into the radial bores 19, 20 of the attachment ring 18 in such a way that the transparent bodies close off the light slits 16, 17 flush in the interior of the tail pipe 15. The operation of flushing with air is dispensed with entirely. The likewise heated transparent bodies are embodied in this case as sapphire disks 58, 59; the sapphire disks 58 disposed in the ceramic body 21 may be embodied as a double cone, to reduce undesirable reflections on the side facing the transmitter wave guide 39. The other sapphire disk 59 in the ceramic body 22 is embodied as a retroreflector 60, which assumes the function of the reflection face 46 in FIG. 1.

To simplify manufacture, the axial bore in the ceramic body 22 is embodied not as a blind bore but rather as a through bore 28'.

The reference diode 56 is disposed not in the receiver 42 but in the transmitter 41, in a side channel downstream, in the transmission direction, of the LED 43, so that the reference diode is likewise acted upon by some of the transmitted light. The reference diode 56 continues to be connected to the evaluation circuit 45. Its purpose is the same, but the third wave guide 47 present in 41 is not needed here.

Instead of the sapphire bars or disks, quartz bars or disks may be used.

Figure 3:
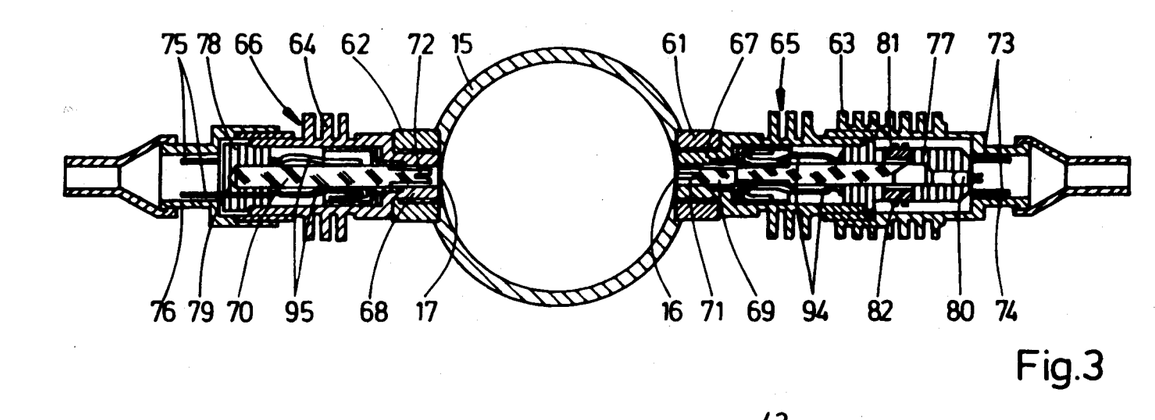
FIG. 3 is a cross section of the exhaust pipe of the exhaust system of a motor vehicle, having a measuring apparatus in a third exemplary embodiment.

The measuring apparatus shown in FIG. 3 is compact in structure and is disposed directly on the tail pipe 15 of the exhaust system of the engine. Two radially offstanding connection necks 61, 62 are welded to the tail pipe 15, surrounding two diametrical openings in the pipe wall. A housing 65 and 66, provided with respective cooling fins 63 and 64, is threaded into each connection neck 61, 62 with an axially protruding, hollow-cylindrical connection tang 67 and 68. The interior openings of the connection tangs 67, 68 form the light slits 16, 17, which are closed off flush by the transparent bodies, in this case embodied as elongated glass rods 69, 70. The glass rods 69, 70, extending axially through each respective housing 65, 66 and made of quartz glass, have a heating coil 71 and 72 on the forward portion of the circumference. Each heating coil 71, 72 is attached directly to the glass rod 69, 70 and insulated with respect to the housing 65 and 66. The electrical contact of the heating coils 71, 72 is effected via spring clamps 94, 95, which press against the heating coil ends and are extended continuously to the rear.

The glass rods 69, 70 are each kept spaced apart from the housing 64, 65, along the end portion remote from the light slits 16, 17, in an axial recess of an insulating block 77 and 78 made of teflon disks. While the end of the glass rod 70 is provided with a retroreflection face 79 that is preferably joined with the glass rod 70 to make a one-piece retroreflector of circular or rectangular cross section, the glass rod 69 is embodied in prismatic fashion, with a rectangular cross-sectional face, as a beam splitter. The LED 80 of the optical transmitter 41, the photoelectric diode 81 and the reference photoelectric diode 82 of the optical receiver 42 are disposed at the end of the beam splitter remote from the light slit 16. These elements are fitted into suitable bores of the insulating block 77 in such a way that the transmission direction of the LED 80 is in alignment with the axis 83 of the glass rod 69, and the receiving directions of the LED 80 and of the photoelectric diode 81 are aligned at right angles to the axis 83 of the rod.

Figure 4:
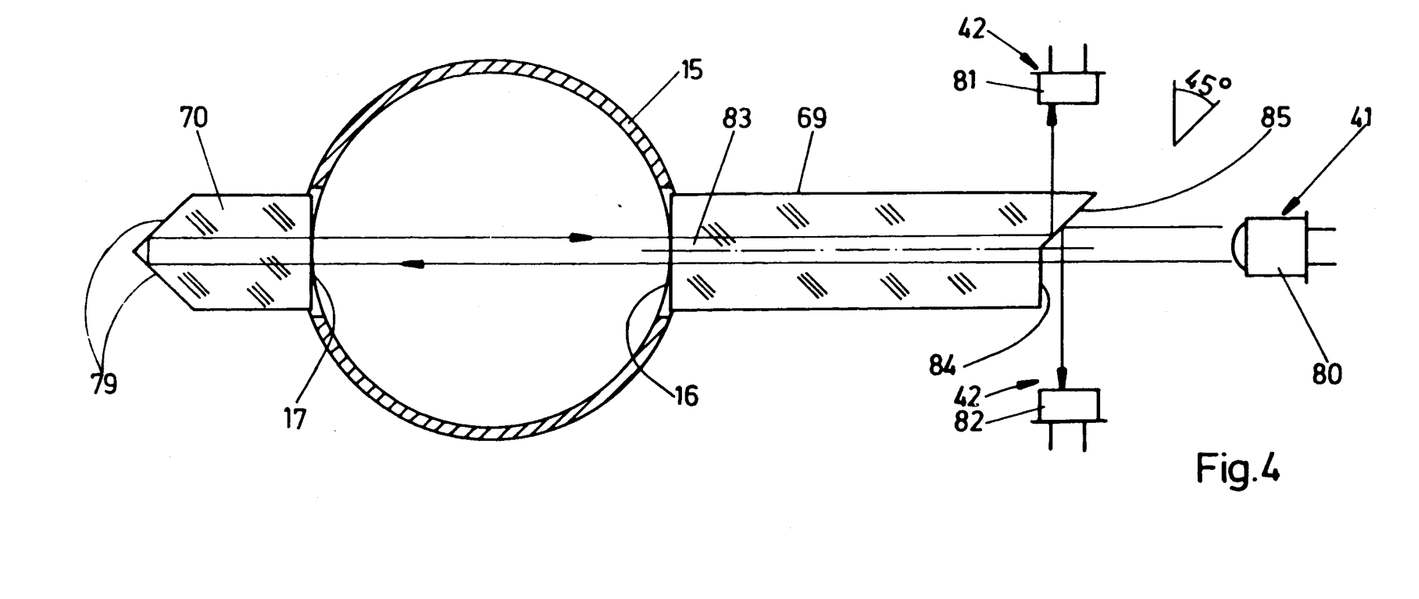
FIG. 4 is an enlarged view of the optical components of the measuring apparatus of FIG. 3.

As can be seen better in the enlarged view of the optical components in FIG. 4, the end face of the glass rod 69 remote from the light slit 16 is divided into a light inlet face 84, extending approximately to the rod axis 83 and extending at right angles to the rod axis 83, and a reflection face 85 extending at an angle of 45° to the rod axis 83.

The photoelectric diode 81 and the reference photoelectric diode 82 face one another on the glass rod 69, so that they are respectively oriented toward the front and back of the reflection face 85. The photoelectric diode 81 is disposed such that the light reflected by the retroreflector 70, 79 is at least partly diverted from the reflection face 85 toward this diode 81, while the reference photoelectric diode 82 is illuminated by some of the transmitted light of the LED 80, reflected by the reflection face 85. The course of the beam of light is represented schematically in FIG. 4. The end face of the glass rod 69 is illuminated by the LED 80. Some of the light is reflected by the reflection face 85 onto the reference photoelectric diode 82. The rest of the light, via the light inlet face 84, enters the glass rod 69, passes through it and the exhaust gas flow in the tail pipe 15, and passes through the glass rod 70, is reflected back by 180° at the retroreflection face of the glass rod 70, passes once again through the glass rod 70 and the exhaust gas flow and the glass rod 69, and is reflected by the reflection face 85 toward the photoelectric diode 81, where the light intensity is measured in the manner described above.

Figure 5:
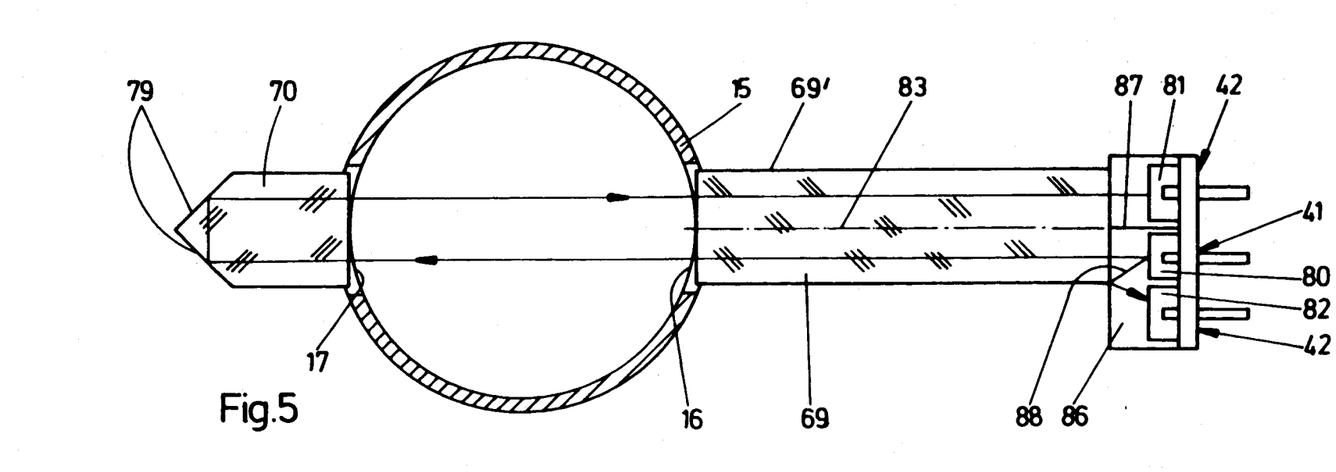
FIGS. 5 and 6 each are a view of a measuring apparatus as in FIG. 4, for a fourth and fifth exemplary embodiment.
Figure 6:
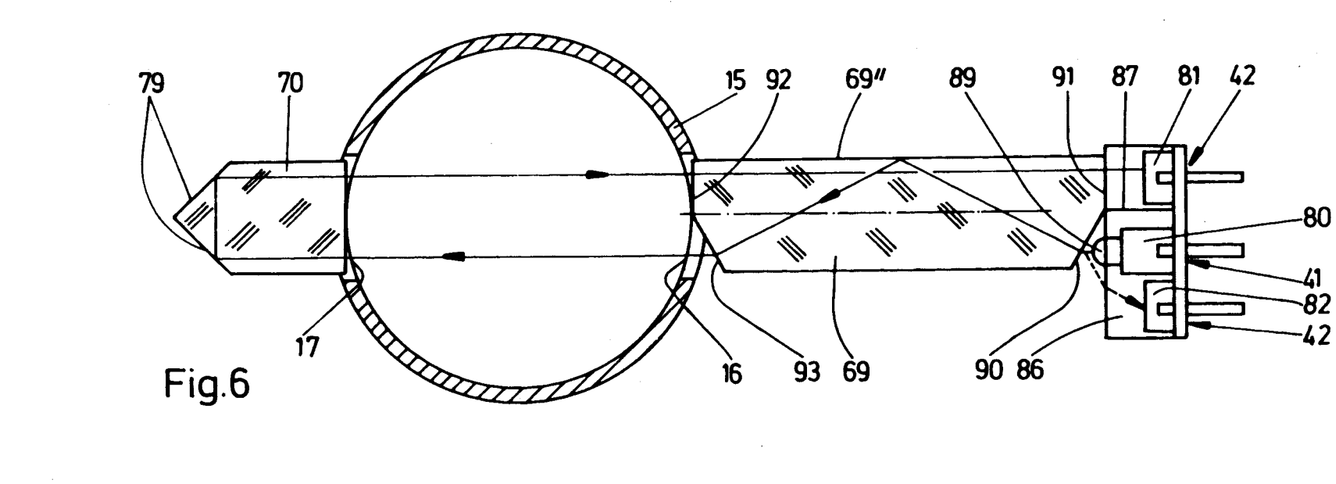

In the exemplary embodiments shown in FIGS. 5 and 6 of the measuring apparatus, the optical component on the transmitter and receiver side is modified. The LED 80 of the optical transmitter 41 and the photoelectric diode 81 and the reference photoelectric diode 82 are disposed on a common substrate 86. This can be done by casting the already manufactured diodes 80-82 together on the substrate 86, or by bonding the semiconductors on the substrate 86. Between the photoelectric diode 81 and the LED 80, a metal wafer 87 is provided for light shielding. The end face of the glass rod 69' remote from the light slit 16 is embodied as flat. The substrate 86 is mounted directly on the end face, and the end face covers the region of the substrate 86 occupied by the photoelectric diode 81 and the LED 80. The region of the substrate 86 that includes the reference photoelectric diode 82 disposed beside the LED 80 is opposite the glass rod 69'. The course of the beam, indicated by arrows in FIG. 5, is once again such that some of the light transmitted by the LED 80 is reflected at the interface between the two optical media and is directed to the reference photoelectric diode 82, while the remainder of the light, after passing twice through the glass rods 69' and 70 and exhaust gas flow, reaches the photoelectric diode 81.

The embodiment of the measuring apparatuses in FIG. 6 differs from that of FIG. 5 in a modified shaping of the glass rod 69''. The LED 80, photoelectric diode 81 and reference photoelectric diode 82 are again accommodated on a common substrate 86, and the LED 80 is flanked by the photoelectric diode 81 and the reference photoelectric diode 82 in the same manner. The photoelectric diode 81 is shielded from the LED 80 by the metal wafer 87. The substrate 86 is again mounted directly on the end face of the glass rod 69'' and extends with about two-thirds of its total area over the end face of the glass rod 69. The LED 80 is opposed by a portion 90 of the end face of the glass rod 69'' that extends approximately as far as the rod axis 83 and is inclined relative to the rod axis 83 by an acute angle. This angle of inclination is adjusted such that some of the light is reflected by the surface portion 90 to the reference photoelectric diode 82, while the majority of the light enters the glass rod 69 at a small angle of incidence. The remaining surface portion 91 of the end face, as before, extends at a right angle to the rod axis 83 and is immediately adjacent the region of the substrate 86 covered by the photoelectric diode 81.

The end face of the glass rod 69'' located at the light slit is also divided into two surface portions 92 and 93. Each surface portion 92, 93 extends as far as the rod axis 83. The surface portion 92 is located opposite the surface portion 91 of the other end face and extends parallel to it, or in other words perpendicular to the rod axis 83. The surface portion 93 is again inclined by an acute angle with respect to the rod axis 83, and the angle of inclination is opposite the angle of inclination of the opposed surface portion 90, but is equal in size. The light exiting from the glass rod 69'' at the surface portion 93 again extends parallel to the rod axis 83, passes through the exhaust gas flow in the tail pipe 15, and enters the glass rod 70 approximately parallel to it axis. After reflection at the retroreflection face 79, the beam of light, now having been deflected twice by 90°, passes through the glass rods 69'', 70 parallel to their axes and finally reaches the photoelectric diode 81. The course of the beam is shown in FIG. 6 by arrows.

The foregoing relates to a preferred exemplary embodiment of the invention, it being understood that other variants and embodiments thereof are possible within the spirit and scope of the invention, the latter being defined by dependent claims.

What is claimed and desired to be secured by Letters Patent of the United States is:

1. An apparatus for measuring a particulate matter in a flue gas or exhaust gas of a combustion process, having an optical transmitter containing a light source for emitting a beam of light to be transmitted to an optical receiver embodied as a photodetector, said beam of light passes through two diametrically opposed light slits in a wall of a tail pipe (15), each slit being closed off by a transparent body embodied as a first glass rod (69) and a second glass rod (70), the light emitted crosses a flow of exhaust gas carried in the exhaust pipe between the opposed light slits, said first and second glass rods (69, 70) including faces which are acted upon by the exhaust gas, and includes means for heating said faces of said transparent bodies to a temperature above a soot burn-off temperature.

2. An apparatus as defined by claim 1, in which said glass rods (69, 70) close off the light slits (16, 17) virtually flush with an inner wall of the tail pipe (15).

3. An apparatus as defined by claim 2, in which said light source is embodied as an LED (80), of said optical transmitter (41) and said optical receiver (42) is a photoelectric diode (81) disposed directly on the first glass rod (69), and a retroreflection face (79) is disposed on a face end remote from the light slit (17) of the second glass rod (70) aligned coaxially with the first glass rod (69), and that the first glass rod (69) is embodied prismatically as a beam splitter, such that the transmitter light reflected by the retroreflection face (79), is at least partly deflected in the first glass rod (69) toward the photoelectric diode (81).

4. An apparatus as defined by claim 3, in which said second glass rod (70) and the retroreflection face (79)

are combined into a one-piece retroreflector of rectangular or circular cross-sectional area.

5. An apparatus as defined in claim 3, in which said optical receiver (42) has a reference photoelectric diode (82), which is disposed directly on the first glass rod (69) in such a way that it is acted upon by some of the transmitter light originating at the LED (80).

6. An apparatus as defined by claim 4, in which said optical receiver (42) has a reference photoelectric diode (82), which is disposed directly on the first glass rod (69) in such a way that it is acted upon by some of the transmitter light originating at the LED (80).

7. An apparatus as defined by claim 5, in which said first glass rod (69) has on its face end remote from the light slit (16) a light inlet face (84) extending approximately as far as and transversely to a rod axis (83), and a reflection face (85) extending approximately as far as the rod axis (83) and at an angle of 45° to it and that the LED (80) is disposed close to this face end, with a transmission direction in alignment with the rod axis (83), and the photoelectric diode (81) and the reference photoelectric diode (82) are also disposed closed to this face end, each with a receiving direction at right angles to the rod axis (83), the photoelectric diode (81) and the reference photoelectric diode (82) facing one another on the first glass rod (69) in such a way that they are oriented toward a front and rear side of the reflection face (85), respectively.

8. An apparatus as defined by claim 5, in which said LED (80), the photoelectric diode (81) and the reference photoelectric diode (82) are disposed with parallel transmission and receiving directions on a substrate (86), the LED (80) being located between the photoelectric diode (81) and the reference photoelectric diode (82), and includes a light shield metal wafer (87), between the LED (80) and the photoelectric diode (81).

9. An apparatus as defined by claim 8, in which an end face of the first glass rod remote from the light slit (16) has a first face portion (91) extending approximately as far as and at right angles to the rod axis (83), this portion being covered directly by the photoelectric diode (81), and a second face portion (90) extending to approximately the rod axis (83) and inclined by an acute angle to it, which portion is illuminated by the LED (80), the angle of inclination of the second face portion (90) being adjusted such that some of the light falling on the second face portion (90) is reflected toward the reference photoelectric diode (82), and that the end face located at the light slit (16) of the first glass rod has a first face portion (92) extending approximately as far as the rod axis (83) and extending parallel to and opposite the first face portion (91) of the first end face, and also has a second face portion (93) extending approximately as far as and at an acute angle with the rod axis (83), the angle of inclination being in the opposite direction of but equal in amount to that of the opposite face portion (90), so that the transmitted light emerging at it extends parallel to the rod axis (83) of the glass rod.

10. An apparatus as defined by claim 4, in which said light slits (16, 17) are each coaxially surrounded by one connection neck (61, 62) welded to the tail pipe (15), that in each connection neck (61, 62) a housing (65, 66) provided with a hollow-cylindrical connection tang (67, 68) is inserted in gas-tight fashion, that the first glass rod (69) and a first heating coil (71), closes off the tang opening and the LED (80), the photoelectric diode (81) and the reference photoelectric diode (82) are disposed in one housing (65), and that the second glass rod (70), embodied as a retroreflector (70, 79) and a second heating coil (72) is disposed in the other housing (66), with a flush closure of the tang opening.

11. An apparatus as defined by claim 10, in which said first and second heating coils (71, 72) are disposed on the first and second glass rods (69, 70) and insulated with respect to the housings (65, 66) and are contacted electrically conductively with terminal connections (94) leading out of the housing.

12. An apparatus as defined by claim 10, in which said housings (65, 66) have radially offstanding cooling fins (63, 64).

13. An apparatus as defined by claim 6, in which said light slits (16, 17) are each coaxially surrounded by one connection neck (61, 62) welded to the tail pipe (15), that in each connection neck (61, 62) a housing (65, 66) provided with a hollow-cylindrical connection tang (67, 68) is inserted in gas-tight fashion, that the first glass rod (69) and a first heating coil (71), closes off the tang opening and the LED (80), the photoelectric diode (81) and the reference photoelectric diode (82) are disposed in one housing (65), and that the second glass rod (70), embodied as a retroreflector (70, 79) and second heating coil (72) is disposed in the other housing (66), with a flush closure of the tang opening.

14. An apparatus as defined by claim 13, in which said first and second heating coils (71, 72) are disposed on the first and second glass rods (69, 70) and insulated with respect to the housings (65, 66) and are contacted electrically conductively with terminal connections (94) leading out of the housing.

15. An apparatus as defined by claim 14, in which said housings (65, 66) have radially offstanding cooling fins (63, 64).

16. An apparatus as defined by claim 7, in which said light slits (16, 17) are each coaxially surrounded by one connection neck (61, 62) welded to the tail pipe (15), that in each connection neck (61, 62) a housing (65, 66) provided with a hollow-cylindrical connection tang (67, 68) is inserted in gas-tight fashion, that the first glass rod (69) and a first heating coil (71), closes off the tang opening and the LED (80), the photoelectric diode (81) and the reference photoelectric diode (82) are disposed in one housing (65), and that the second glass rod (70), embodied as a retroreflector (70, 79) and second heating coil (72) is disposed in the other housing (66), with a flush closure of the tang opening.

17. An apparatus as defined by claim 16, in which said first and second heating coils (71, 72) are disposed on the first and second glass rods (69, 70) and insulated with respect to the housings (65, 66) and are contacted electrically conductively with terminal connections (94) leading out of the housing.

18. An apparatus as defined by claim 17, in which said housings (65, 66) have radially offstanding cooling fins (63, 64).

19. An apparatus as defined by claim 8, in which said light slits (16, 17) are each coaxially surrounded by one connection neck (61, 62) welded to the tail pipe (15), that in each connection neck (61, 62) a housing (65, 66) provided with a hollow-cylindrical connection tang (67, 68) is inserted in gas-tight fashion, that the first glass rod (69) and a first heating coil (71), closes off the tang opening and the LED (80), the photoelectric diode (81) and the reference photoelectric diode (82) are disposed in one housing (65), and that the second glass rod (70), embodied as a retroreflector (70, 79) and second heating coil (72) is disposed in the other housing (66), with a flush closure of the tang opening.

20. An apparatus as defined by claim 19, in which said first and second heating coils (71, 72) are disposed on the first and second glass rods (69, 70) and insulated with respect to the housings (65, 66) and are contacted electrically conductively with terminal connections (94) leading out of the housing.

21. An apparatus as defined by claim 20, in which said housings (65, 66) have radially offstanding cooling fins (63, 64).

* * * * *